United States Patent
Veronesi

(10) Patent No.: US 6,855,835 B2
(45) Date of Patent: Feb. 15, 2005

(54) ALLOMORPH OF ISOMER Z HYDROCHLORIDE OF ALKYLAMINOFURANE DERIVATIVE

(75) Inventor: Paolo Alberto Veronesi, Milan (IT)

(73) Assignee: Pharmexcel SRL, Milan (IT)

( * ) Notice: Subject to any disclaimer, the term of this patent is extended or adjusted under 35 U.S.C. 154(b) by 14 days.

(21) Appl. No.: 10/232,859

(22) Filed: Aug. 29, 2002

(65) Prior Publication Data

US 2004/0048922 A1 Mar. 11, 2004

Related U.S. Application Data

(63) Continuation of application No. PCT/EP01/02226, filed on Feb. 27, 2001.

(30) Foreign Application Priority Data

Feb. 29, 2000 (IT) .................................... MI2000A0376

(51) Int. Cl.$^7$ .................... C07D 307/52; C07D 307/34; A61K 31/341
(52) U.S. Cl. ....................... 549/495; 514/471
(58) Field of Search ........................... 549/495; 514/471

(56) References Cited

U.S. PATENT DOCUMENTS

| | | | |
|---|---|---|---|
| 4,672,133 A | 6/1987 | Crookes | 549/495 |
| 5,663,381 A | 9/1997 | Schickaneder et al. | 549/492 |

FOREIGN PATENT DOCUMENTS

| | | |
|---|---|---|
| DE | 31 39 134 A1 | 5/1982 |
| EP | 0 626 381 A1 | 11/1994 |

OTHER PUBLICATIONS

Cholerton, Trevor J. et al., "Spectroscopic Studies on Ranitidine—its Structure and the Influence of Temperature and pH", *J. Chem. Soc. Perkin Trans.*, No. II, 1984, pp. 1761–1766. (XP–001007750).

Enriz, R. D. et al., "Empirical Atom–Atom Potential Calculations On Two Antagonist In Histamine H2–Receptors: Rantitidine and Etinidine", *Acta Cientifica Venezolana*, No. 39, 1988, pp. 214–223. (XP–001005561).

Forster, Angus et al., "Characterization of two polymorphic forms of Ranitidine–HCl", *The Internet Journal of Vibrational Spectroscopy*, vol. 2, Edition 2, 1989, 6 pages. (XP–002171376).

Seddon, Kenneth R., "Crystal Engineering", *Crystal Engineering: The Design and Application of Functional Solids*, published 1999, pp. 1–28. (XP–001007665).

Wu, V. et al., "Stability of polymorphic forms of rantitidine hydrochloride", *Pharmazie*, No. 55, vol. 7, 2000, pp. 508–512. (XP–000999403).

*Primary Examiner*—Ba K. Trinh
(74) *Attorney, Agent, or Firm*—Steven P. Shurtz; Brinks Hofer Gilson & Lione

(57) ABSTRACT

Allomorph of Z isomer of N-[2-[[[5-(dimethylamino) methyl-2-furanyl]methyl]thio]ethyl]-N'-methyl-2-nitro-1,1-ethenediamine hydrochloride, with two carbon atoms linked by a rigid ethylenic bond, marked by an asterisk (*), characterized by the following structural formula:

(II)

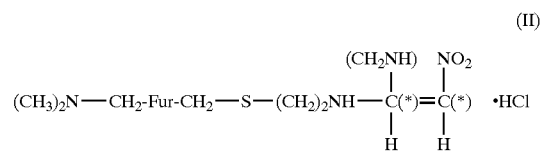

wherein -Fur- represents a furane ring.

9 Claims, 2 Drawing Sheets

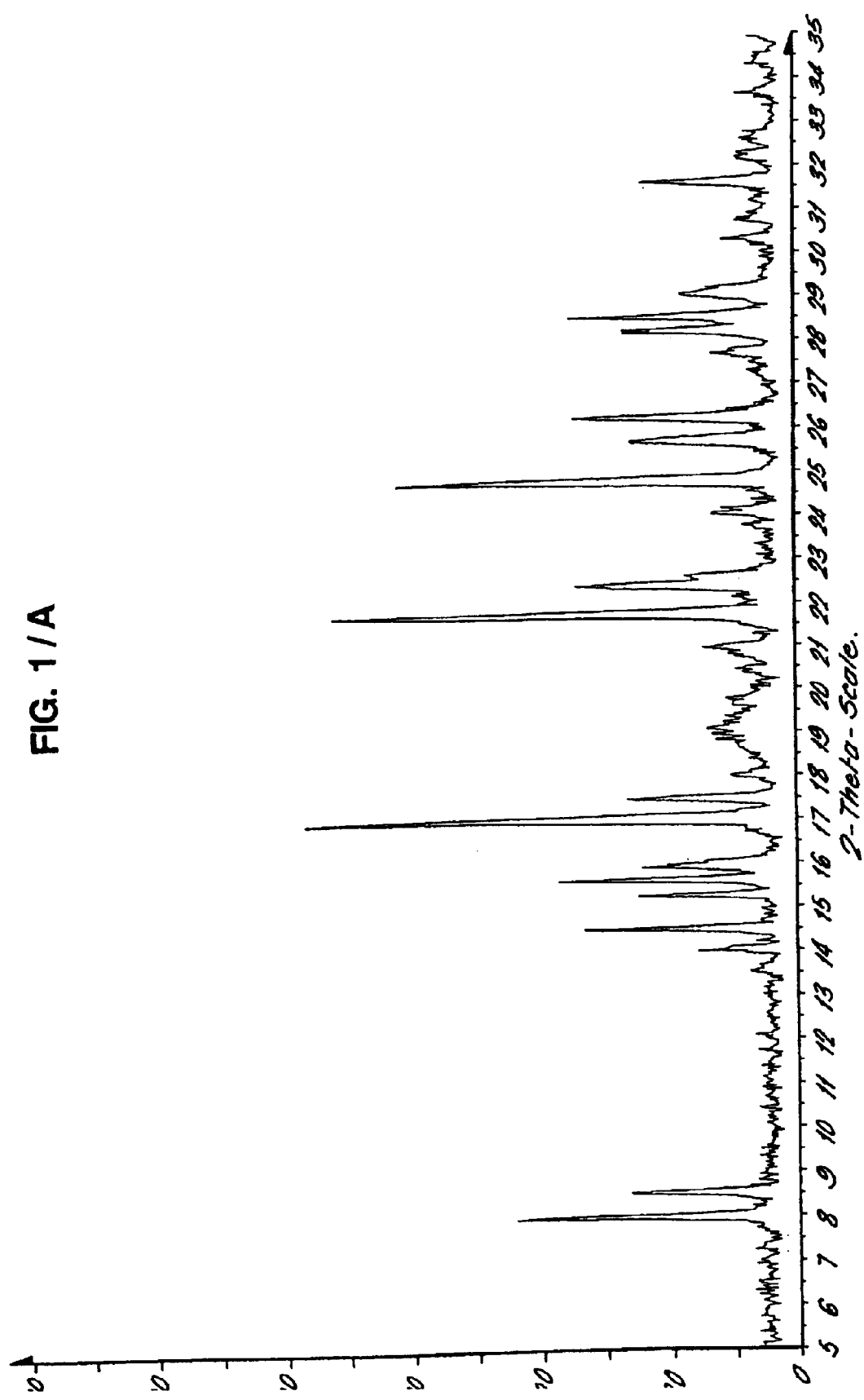
FIG. 1/A

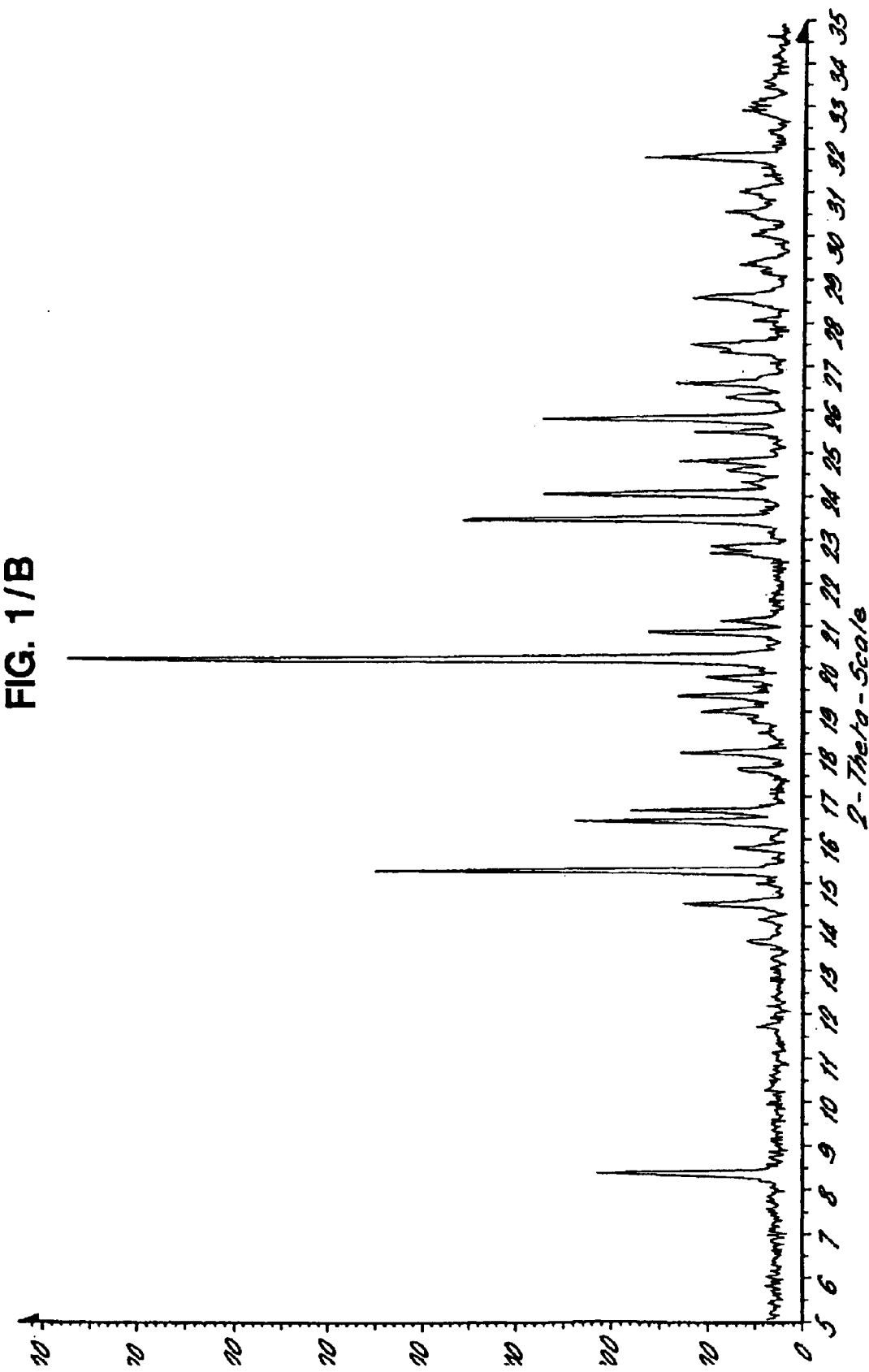
FIG. 1/B

ALLOMORPH OF ISOMER Z HYDROCHLORIDE OF ALKYLAMINOFURANE DERIVATIVE

REFERENCE TO EARLIER FILED APPLICATIONS

The present application is a continuation of and claims the benefit of the filing date under 35 U.S.C. §120 of PCT Application Serial No. PCT/EP01/02226, filed Feb. 27, 2001, published as WO 01/64662, designating the United States, which in turn claims priority to Italian Patent Application M1 2000A 000376, filed Feb. 29, 2000, both of which are hereby incorporated by reference.

The invention relates to the allomorph of Z isomer of N-[2-[[[5-(dimethylamino)methyl-2-furanyl]methyl]thio] ethyl]-N'-methyl-2-nitro-1,1-ethenediamine hydrochloride, the procedure of its production and the pharmaceutical composition which contains it.

In order to better illustrate, appreciate and characterize the teachings of the invention in relationship with the state-of-the-art, we have listed in the paragraph headed "References" the most significant bibliography concerning this subject matter.

BRIEF DESCRIPTION OF THE DRAWINGS

FIG. 1/A shows an X-ray diffraction pattern of allomorph (A) of the Z isomer of N-2-[[[5-(dimethylamino)methyl-2-furanyl]methyl ]thio]ethyl]-N'-methyl-2-nitro-1,1-ethenediamine hydrochloride.

FIG. 1/B shows an X-ray diffraction pattern of allomorph (B) of the Z isomer of N-[2-[[[5-(dimethylamino)methyl-2-furanyl]methyl]thio]ethyl]-N'-methyl-2-nitro-1,1-ethenediamine hydrochloride.

The present invention is characterized by the fact that various allomorphs of Z isomer of N-[2-[[[5-(dimethylamino)methyl-2-furanyl]methyl]thio]ethyl]-N'-methyl-2-nitro-1,1-ethenediamine hydrochloride, hereinafter defined more simply as allomorphs of Z, N-[2-[[[5-(dimethylamino)methyl-2-furanyl]methyl]thio]ethyl]-N'-methyl-2-nitro-1,1-ethenediamine hydrochloride, are manufactured and isolated by a synthesis process which uses as starting intermediate exclusively the Z isomer of N-[2-[[[5-(dimethylamino)methyl-2-furanyl]methyl]thio]ethyl]-N'-methyl-2-nitro-1,1-ethenediamine, which, in turn, is characterized as it is obtained by a special selective synthesis, which uses as starting material the Z isomer of N-methyl-1-(methylthio)-2-nitroethenamine.

Another particular aspect of the invention is that Z isomer of N-methyl-1-(methylthio)-2-nitroethenamine is not obtained by conventionally known methods (1, 2, 3), which requires generally the treatment with the methylamine of 1,1-bis(methylthio)-2-nitroethene, at different conditions, but it may be produced by other selective syntheses (4) enabling to obtain exclusively the Z isomer of the above intermediate. For a better understanding of the invention, we show here below the structural formula of Z isomer of N-methyl-1-(methylthio)-2-nitroethenamine (I):

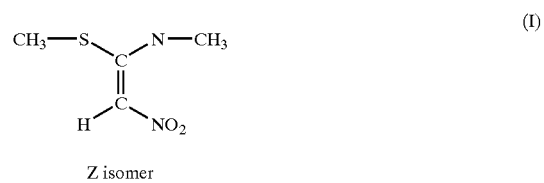

Z isomer

Though in the past this aspect was scarcely known (it could be better to say that it has been totally ignored, in spite of the potential remarkable implications of toxicologic, pharmacologic and clinical nature), N-[2-[[[5-(dimethylamino)methyl-2-furanyl]methyl]thio]ethyl]-N'-methyl-2-nitro-1,1-ethenediamine hydrochloride exhibits the phenomenon of geometric isomerism. Therefore, if a particular selective synthesis is not adopted for the preparation of the base substance (N-[2-[[[5-(dimethylamino) methyl-2-furanyl]methyl]thio] ethyl]-N'-methyl-2-nitro-1, 1-ethenediamine) used for its synthesis, the resulting hydrochloride unavoidably appears as a racemic mixture of E and Z isomers, which are present in a not well defined ratio. Since the invention concerns only and in particular the allomorph of Z, N-[2-[[[5-(dimethylamino)methyl-2-furanyl]methyl]thio]ethyl]-N'-methyl-2-nitro-1,1-ethenediamine hydrochloride, the procedure for its production and the pharmaceutical composition which contains it, for a better clarity and understanding of the invention, we show here below the corresponding structural formula in which the two ethylenic carbon atoms are marked by an asterisk (*), which are linked by a double bond (rigid) and give way to the above mentioned geometric isomerism, and we send on the contrary to another later section the discussion of its allomorphic forms:

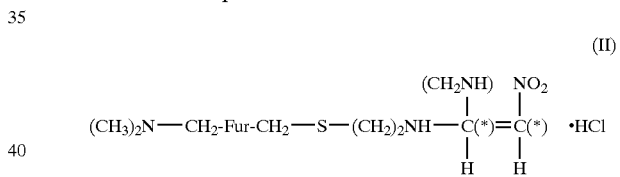

(Z, (N-[2-[[[5-(dimethylamino)methyl-2-furanyl]methyl] thio]ethyl]-N'-methyl-2-nitro-1,1-ethenediamine) hydrochloride) where Fur=furane ring.

Moreover, the experts know very well that, since its first description, N-[2-[[[5-(dimethylamino)methyl-2-furanyl] methyl]thio]ethyl]-N'-methyl-2-nitro-1,1-ethenediamine hydrochloride (5, 6, 7, 8, 9), both as polymorph form 1 (7, 8, 9) and exclusively as polymorph form 2 (6), has been employed in human medicine for its properties of antagonist of histamine $H_2$-receptors and, thus, as a medicinal substance active against gastroduodenal ulcer only and exclusively in the racemic form, or rather as a mixture of the two possible geometric E and Z isomers, which originate indifferently in the course of any procedure of a non-selective synthesis. Indeed, at the state-of-the-art, nobody claimed or described the ratio of two E and Z isomers of N-[2-[[[5-(dimethylamino)methyl-2-furanyl]methyl]thio] ethyl]-N'-methyl-2-nitro-1,1-ethenediamine or of its hydrochloride in the different racemic mixtures, which are available on the market, and are used as such without any special cautiousness. Moreover, no special procedure of selective synthesis was described, which could yield a particular type of isomer and so far no method is known which enables to separate on an industrial scale from these racemic mixtures the two E and Z isomers of N-[2-[[[5-(dimethylamino)methyl-2- furanyl]methyl]thio]ethyl]-N'-methyl-2-nitro-1,1-ethenediamine or of its hydrochloride salt.

This latter possibility, although it could be hypothetically feasible at a laboratory scale, would result in practice uneconomic and therefore not feasible for industrial and trade purposes, for which huge amounts of the product and the need of containing the manufacturing costs are necessary. Indeed, these costs would rise tremendously if one of the two isomers should be removed. Indeed, some authors (10, 11) have surprisingly suggested in recent studies a greater configurational affinity of Z isomer of N-[2-[[[5-(dimethylamino)methyl-2-furanyl]methyl]thio]ethyl]-N'-methyl-2-nitro-1,1-ethenediamine for histamine $H_2$-receptors and have thus found a higher degree of specific antagonism on them, which are supported by complex measurements of conformational energy.

Therefore, a surprising and important application of the invention is that the allomorph of Z, N-[2-[[[5-(dimethylamino)methyl-2-furanyl]methyl]thio]ethyl]-N'-methyl-2-nitro-1,1-ethenediamine hydrochloride could elicit a greater affinity for histamine $H_2$-receptors and, thus exert a greater antagonistic activity.

This detail of not negligible importance, which will be matter of further verifications and investigations of biochemical and pharmacological nature, could also contribute to clear two worrying aspects so far still unsolved:

(a) to enable to reduce the administered doses of allomorph of Z aminoalkylfurane hydrochloride derivative, which, due to its greater affinity for histamine $H_2$-receptors, could enable to elicit a pharmacologic response of equal or higher intensity even at very lower doses;

(b) to avoid the administration of E isomer, which, due to its geometric configuration, besides being less active, perhaps could be more oxidizable at the level of "N'-methyl" group, thus resulting more easily convertible into the corresponding nitrosamine.

Indeed, it is well known that nitrosamines are responsible for the onset of cancerogenesis processes (12, 13, 14, 15, 16).

Concerning this second aspect, indeed, the wide literature published in the more recent years is very alarming (17, 18, 19, 20, 21, 22). Indeed, it shows a constant increase in cases of gastric cancer, but without finding its correlation, in patients treated with ethical drugs containing the common ranitidine hydrochloride (racemic) (N-[2-[[[5-(dimethylamino)methyl-2-furanyl]methyl]thio]ethyl]-N'-methyl-2-nitro-1,1-ethenediamine hydrochloride) (6).

If actually E isomer of N-[2-[[[5-(dimethylamino)methyl-2-furanyl]methyl]thio]ethyl]-N'-methyl-2-nitro-1,1-ethenediamine should be more easily convertible into the corresponding nitrosamine by biologic oxidation, following the oral administration of the above mentioned drug, it would be rather necessary to entirely remove the E isomer from the product.

Another scientific source (23) has established that Z isomer of N-[2-[[[5-(dimethylamino)methyl-2-furanyl]methyl]thio]ethyl]-N'-methyl-2-nitro-1,1-ethenediamine, could exhibit by contrast a more stable isomeric configuration, perhaps less predisposed to the aggression of oxygen, therefore, less convertible into nitrosamine, due to that Z isomer, when in water solution, has the tendency to yield a cyclization, which could make less probable any oxidation of this radical.

It is worth to remind the presumably similar case of tamoxifen, a molecule which also shows a geometric isomerism, in which Z isomer alone is the true active substance against the tumoral cells (Z-tamoxifen is indicated in the prevention and treatment of breast cancer), whereas it has been proven that the other E isomer shows even a mutagenic activity (24, 25, 26).

Therefore, the immediate consequence of all above observations is that surprisingly, from the performed studies, Z isomer of N-[2-[[[5-(dimethylamino)methyl-2-furanyl]methyl]thio]ethyl]-N'-methyl-2-nitro-1,1-ethenediamine seems to exhibit a greater affinity for histamine $H_2$-receptors, thus a greater anti-histaminic activity than E isomer.

Another surprising embodiment of the invention is that, in order to obtain allomorph of Z isomer of N-[2-[[[5-(dimethylamino)methyl-2-furanyl]methyl]thio]ethyl]-N'-methyl-2-nitro-1,1-ethenediamine hydrochloride, it is necessary to find an industrial process of selective synthesis enabling to produce remarkable amounts of Z isomer of N-[2-[[[5-(dimethylamino)methyl-2-furanyl]methyl]thio] ethyl]-N'-methyl-2-nitro-1,1-ethenediamine. This problem has been advantageously resolved by the invention.

Another surprising aspect of the invention is that the selective synthesis of Z isomer was found by using as starting material the Z isomer of N-methyl-1-methylthio-2-nitroetheneamine.

Another aspect of the invention is that, by transforming Z isomer of N-[2-[[[5-(dimethylamino)methyl-2-furanyl]methyl]thio]ethyl]-N'-methyl-2-nitro-1,1-ethenediamine into its hydrochloride salt by applying a particular and innovative manufacturing procedure, the hydrochloride of the above mentioned Z isomer may be obtained as a more convenient and more formulable powder, as technico-pharmaceutical point of view, so that it is possible to obtain both allomorphs (A) and (B) of said hydrochloride.

Indeed, the above mentioned product is not available nowadays at the state-of-the-art since no patent has described or claimed any specific isomer of N-[2-[[[5-(dimethylamino)methyl-2-furanyl] methyl] thio]ethyl]-N'-methyl-2-nitro-1,1-ethenediamine or its hydrochloride. Similarly no method of selective synthesis was ever described, claimed or published which, starting from Z isomer of N-methyl-1-(methylthio)-2-nitroethenamine, could lead to obtain Z isomer of N-[2-[[[5-(dimethylamino) methyl-2-furanyl]methyl]thio]ethyl]-N'-methyl-2-nitro-1,1-ethenediamine nor any polymorphous forms of the corresponding hydrochloride.

By contrast to the absolute indifference which always accompanied the phenomenon of geometric isomerism of N-[2-[[[5-(dimethylamino)methyl-2-furanyl]methyl]thio] ethyl]-N'-methyl-2-nitro-1,1-ethenediamine and its hydrochloride, at the beginning of the eighties, it was emphasized, in a disproportionate nearly triumphalistic way, that hydrochloride of N-[2-[[[5-(dimethylamino)methyl-2-furanyl]methyl]thio]ethyl]-N'-methyl-2-nitro-1,1-ethenediamine—probably consisting of a racemic mixture in the absence of special references pointing to a particular isomer—form 2 could be obtained as new polymorphous crystalline form, which was also a matter of specific patent protection (6). This form 2 was defined as a remarkable improvement of an identical molecule (N-[2-[[[5-(dimethylamino)methyl-2-furanyl]methyl]thio]ethyl]-N'-methyl-2-nitro-1,1-ethenediamine hydrochloride), which was claimed some years before, and now named by contrast form 1. Form 2 was then characterized by the inventors, in relationship with the previous form 1, "by its infrared spectrum in mineral oil and/or by its scheme of X-rays diffraction of the powder".

Moreover, form 2 of the above mentioned compound (presumably always consisting of the racemic mixture of geometric isomers), is claimed in some publications as it were "a new form of a substance", and in the description it is mentioned that "it is less hygroscopic than form 1, which represents an additional advantage, due to the sensitivity of ranitidine hydrochloride to moisture".

By contrast with the above, namely, the present invention concerns the allomorph of Z isomer of N-[2-[[[5-(dimethylamino)methyl-2-furanyl]methyl]thio]ethyl]-N'-methyl-2-nitro-1,1-ethenediamine hydrochloride, which is obtained according to the following original manufacturing schemes:

Scheme 1
Preparation of Z, N-[2-[[[5-(dimethylamino)methyl] 2-furanyl]methyl] thio]ethyl]-N'-methyl-2-nitro-1,1-ethenediamine $(CH_3NH)(CH_3S)C=CHNO_2$ +
(I) Z isomer
$(CH_3)_2N-CH_2-Fur-CH_2-S-(CH_2)_2NH_2$ ---->
(III)

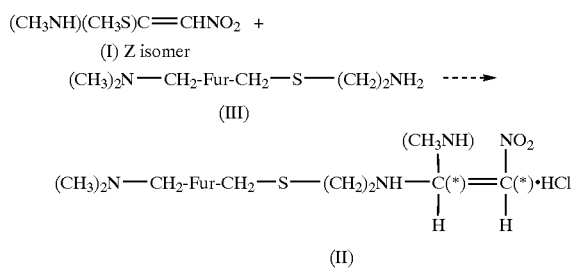

(II)

(II)=Z, (N-[2-[[[5-(dimethylamino)methyl-2-furanyl] methyl]thio] ethyl]-N'-methyl-2-nitro-1,1-ethenediamine)
wherein:
(I) Z isomer=Z, N-methyl-1-(methylthio)-2-nitroethenamine (intermediate available on the market or obtainable by already known processes)
Fur=furane ring
(III)=2-[[[5-(dimethylamino)methyl-2-furanyl]methyl] thio]-ethenamine The conventional synthesis, already described in the literature, differs from Scheme 1, since this latter uses exclusively as starting intermediate of synthesis the Z isomer of N-methyl-1-(methylthio)-2-nitroethenamine ((I)=Z isomer). However, intermediate (III) is commonly available on the market and obtainable by already known processes.

Scheme 2
Preparation of allomorph (A) of Z, N-[2-[[[5-(dimethylamino)methyl-2-furanyl]methyl]thio]ethyl]-N'-methyl-2-nitro-1,1-ethenediamine hydrochloride.

$(CH_3)_2N-CH_2-Fur-CH_2-S-(CH_2)_2NH-C(NHCH_3)=CHNO_2$ +
(II) Isomer Z

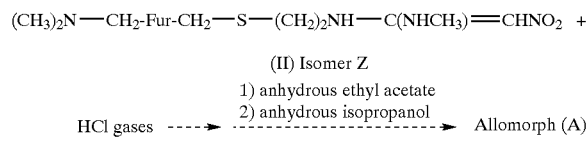

of Z, N-[2-[[[5-(dimethylamino)methyl-2-furanyl]methyl] thio]ethyl]-N'-methyl-2-nitro-1,1-ethenediamine hydrochloride.

In scheme 2 Z, N-[2-[[[5-(dimethylamino)methyl-2-furanyl]methyl] thio]ethyl]-N'-methyl-2-nitro-1,1-ethenediamine is uniformly suspended in rigorously anhydrous ethyl acetate and is reacted under constant stirring with a solution of hydrochloric acid in anhydrous isopropanol at a concentration ranging from 2.0% to 12.0%, preferably of about 10%, added dropwise to the first one dropwise, thus obtaining a white precipitate consisting of crystals of allomorph (A) of Z, N-[2-[[[5-(dimethylamino) methyl-2-furanyl]methyl]thio]ethyl]-N'-methyl-2-nitro-1,1-ethenediamine hydrochloride, which are collected, washed at first with an anhydrous mixture of ethyl acetate and isopropanol and then with anhydrous ethyl acetate alone and, finally dried by using traditionally known procedures (in-vacuo, under nitrogen flow, at a temperature lower than 30° C.).

The crystallographic analysis, carried out with an already known method reported in a previous patent (6), shows a scheme of X-ray diffraction (FIG. 1/A) which confirms that allomorph (A) of Z, N-[2-[[[5-(dimethylamino)methyl-2-furanyl]methyl]thio]ethyl]-N'-methyl-2-nitro-1,1-ethenediamine hydrochloride has been found.

Scheme 3
Preparation of allomorph (B) of Z, N-[2-[[[5-(dimethylamino)methyl-2-furanyl]methyl]thio]ethyl]-N'-methyl-2-nitro-1,1-ethenediamine hydrochloride $(CH_3)_2N-CH_2-Fur-CH_2-S-(CH_2)_2NH-C(NHCH_3)=CHNO_2$ +
(II) Isomer Z

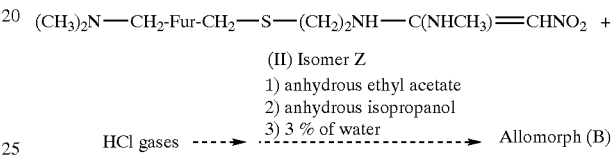

of Z, N-2-[[[5-(dimethylamino)methyl-2-furanyl]methyl] thio]ethyl]-N'-methyl-2-nitro-1,1-ethenediamine hydrochloride.

In Scheme 3 Z, N-[2-[[[5-(dimethylamino)methyl-2-furanyl]methyl] thio]ethyl]-N'-methyl-2-nitro-1,1-ethenediamine is uniformly suspended in ethyl acetate and reacted under constant stirring with a solution of hydrochloric acid in isopropanol, added with 3% of water, at a concentration ranging from 2.0% to 12.0%, preferably about 10%, added dropwise to the first one, thus obtaining a white precipitate consisting of crystals of allomorph (B) of Z, N-[2-[[[5-(dimethylamino)methyl-2-furanyl]methyl]thio] ethyl]-N'-methyl-2-nitro-1,1-ethenediamine hydrochloride, which are collected, washed at first with an anhydrous mixture of ethyl acetate and isopropanol and then with anhydrous ethyl acetate alone and finally dried by procedures already known to the experts (in-vacuo, under nitrogen flow, at a temperature lower than 30° C.).

The crystallographic analysis, carried out with an already known method and described in a previous patent (6), exhibits a scheme of X-ray diffraction (FIG. 1/B) which confirms that it is an allomorph (B) of Z, N-[2-[[[5-(dimethylamino)methyl-2-furanyl]methyl]thio] ethyl]-N'-methyl-2-nitro-1,1-ethenediamine hydrochloride.

In a similar way, if in Scheme 1 a racemic mixture of N-methyl-1-(methylthio)-2-nitroethenamine is used (instead of isomer Z alone of the same intermediate), the resulting N-[2-[[[5-(dimethylamino)methyl-2-furanyl]methyl]thio] ethyl]-N'-methyl-2-nitro-1,1-ethenediamine will consist of a racemic mixture of E and Z isomers.

Likewise, using Schemes 2 and 3 of the invention, it is possible however to obtain the relevant allomorphs (A) and (B) of N-[2-[[[5-(dimethylamino)methyl-2-furanyl]methyl] thio]ethyl]-N'-methyl-2-nitro-1,1-ethenediamine hydrochloride, in the form of racemic mixture.

Although the allomorphs of hydrochloride salt of these racemic mixtures are obtained with original new methods, which may be applied on an industrial scale, they are not claimed in the present invention, which more specifically concerns allomorphs (A) and (B) of Z, N-2-[[[5-(dimethylamino)methyl-2-furanyl]methyl]thio]ethyl]-N'- methyl-2-nitro-1,1-ethenediamine hydrochloride, which is the subject matter of the present invention.

Crystalline powders of allomorphs (A) and (B) of the invention exhibit rather similar characteristics. Therefore, they can be used indifferently to develop pharmaceutical preparations of the invention, to be used in human medicine for the management of gastrointestinal ulcers and of other similar pathologic conditions.

The allomorph of the invention may be formulated for the administration in any convenient way and therefore the present invention includes pharmaceutical compositions containing indifferently allomorphs (A) or (B) of the invention.

These compositions may be presented, depending on their use, in a convenient manner, with the aid of a vehicle, support or excipient which are pharmaceutically acceptable and compatible with the allomorph and which may also contain, if necessary, other active ingredients, as an example particular antibiotic or chemoterapeutic agents, which is especially useful if employed in combination for the eradication of *Helicobacter pylori* or of other similar species.

Therefore, the allomorph of the invention may be formulated for oral administration, preferably as tablets, lozenges and hard and soft gelatin capsules.

For the oral administration of the allomorph of the invention, the pharmaceutical composition could also be powder, solution, syrup or suspension, prepared by known procedures, with pharmaceutically acceptable excipients.

The allomorph of the invention may be advantageously formulated also for the parenteral administration, by continuous intravenous infusion or bolus. The formulations for injection, usually in the form of individual dose, are prepared in a rigorously sterile form in ampoules sealed at their upper side or in glass vials with perforable stopper and aluminum ring. Water is the preferred vehicle to this purpose. Other compatible formulating excipients may be added to water, such as stabilizing or dispersing agents.

In relation to the regimen of convenient daily dosing of the allomorph of the invention, the amounts per unit dose could vary depending on the route of administration, on their frequency and patient's health conditions.

However, in view of the probable higher affinity, resulting from specialized publications, of the allomorph of the invention for histamine $H_2$-receptors, it may be expected that these compounds could exert, at the same dose, a more marked antagonistic activity, which could also take to the adoption of lower doses than those used at present for the common racemate.

REFERENCES

The publications are mentioned in the description with the same progressive number assigned in this list.

(1) GB No. 2230526 assigned to Fine Organics Ltd, transferred to Glaxo Group Ltd;
(2) ES No. 523448 assigned to Union Quimica Farmaceutica SA;
(3) GB No. 2160204, assigned to Glaxo Group Ltd;
(4) GB No. 1554153, assigned to Smith Kline and French Laboratories Ltd;
(5) Italian patent No. 1.126.759 (priority GB N. 1,565,966) assigned to Allen & Hamburys Ltd.;
(6) Italian patent No. 1.143.237 (priority GB N. 2,084,580) assigned to Glaxo Group Ltd.;
(7) EP No. 0 626 381 B1 assigned to Torcan Chem. Ltd.;
(8) U.S. Pat. No. 5,663,381 assigned to Hexal Pharm., Inc.;
(9) WO 95/28918 (priority DK 0468/94 filed on 22.04.94) assigned to Gea Farmaceutisk Fabrik;
(10) Enriz R. D., Ciuffo G. M., Estrada M. R., Jáurequi E. A.: "Empirical atom-atom potential calculations on two antagonists in histamine $H_2$-receptors: ranitidine and etintidine". Acta Cient Venez 39: 214–223, 1988.
(11) Enriz D. R., Jáurequi E. A.: "Estudio teorico conformational de tiotidina y nizatidina, dos potentes antagonistas en los receptores $H_2$ de histamina". Acta Cient Venez 42: 70–76, 1991.
(12) Brown J L: "N-Nitrosamines". Occup Med 14(4): 839–48, 1999.
(13) Gurski R R, Schirmer C C, Kruel C R, Komlos F, Kruel C D, Edelweiss M I: "Induction of esophageal carcinogenesis by diethylnitrosamine and assessment of the promoting effect of ethanol and N-nitrosonornicotine: experimental model in mice". Dis Esophagus 12(2): 99–105, 1999.
(14) Hecht S S: "Tobacco smoke carcinogens and lung cancer". J Natl Cancer Inst 91(14): 1194–210.
(15) Hiasa Y, Paul M, Hayashi I, Mochizuki M, Tsutsumi H, Kuwashima S, Kitahori Y, Konishi N: "Carcinogenic effects of N-ethyl-N-hydroxyethylnitrosamine and its metabolites in rats and mice". Cancer Lett 145(1–2): 143–9, 1999.
(16) Mitacek E J, Brunnemann K D, Suttajit M, Martin N, Limsila T, Ohshima H, Caplan L S: "Exposure to N-nitroso compounds in a population of high liver cancer regions in Thailand: volatile nitrosamine (VNA) levels in Thai food". Food Chem Toxicol 37(4): 297–305, 1999.
(17) Van Vlierberghe H: "Fundic gland polyps: three other case reports suggesting a possible association with acid suppressing therapy". Acta Gastoenterol Belg. 60(3)-240–2, 1997.
(18) Johnson A G: "Histamine-2 receptor antagonists and gastric cancer". Epidemiology 7(4): 434–6, 1996.
(19) Wood J R: "Gastric carcinoid associated with ranitidine and renal failure". Am J Gastroenterol 89(2): 285–7, 1994.
(20) La Vecchia C.: "Histamine-2-receptor antagonists and gastric cancer risk". Lancet 336(98711): 355–7, 1990.
(21) Havu N.: "Enterochromaffin-like cell carcinoids in the rat gastric mucosa following long-term administration of ranitidine". Digestion 45(4): 189–95, 1990.
(22) Mignon M: "Development of gastric argyrophyl carcinoid tumors in a case of Zollinger-Ellison syndrome with primary hyperparathyroidism during long-term antisecretory treatment". Cancer 59 (11): 1959–62, 1987.
(23) Cholerton T J, Hunt J H, Klinkert G, Martin-Smith M: "Spectroscopic studies on ranitidine—its structure and the influence of temperature and pH". J Chem Soc Perkin Trans, II: 1761–66, 1984.
(24) Brown K: "Determination of damage in F344 rats induced by geometric isomers of tamoxifen and analogues". Chem res Toxicol 11(5): 527–35, 1998.
(25) Pongracz K: "Activation of the tamoxifen derivative metabolite E to form DNA adducts: comparison with the adducts formed by microsomal activation of tamoxifen". Cancer Res 55(14): 3012–5, 1995.
(26) Robertson D W: "Tamoxifen antiestrogens. A comparison of the activity, pharmacokinetics, and metabolic activation of the cis and trans isomers of tamoxifen". J Steroid Biochem 16(1): 1–13, 1982.

Moreover, the invention is better described by the following examples. However, these examples are not a limit of the subject matter of the invention itself.

EXAMPLE 1

Preparation of Allomorph (A) of Z, N-[2-[[[5-(dimethylamino)methyl-2-furanyl]methyl]thio]ethyl]-N'- methyl-2-nitro-1,1-ethenediamine Hydrochloride. Under conditions of inert atmosphere, saturated with nitrogen, suspend 10.0 g of Z, N-[2-[[[5-(dimethylamino)methyl-2-furanyl]methyl]thio]ethyl]-N'-methyl-2-nitro-1,1-ethenediamine in 100 ml of anhydrous ethyl acetate (moisture<0.01%). Add dropwise to the mixture 21.95 g of hydrochloric acid in isopropanol (concentration 5.29% mol/mol) during 45 minutes, keeping the temperature at 25° C. Stirring vigorously, again in inert nitrogen atmosphere, a white precipitate is obtained. By operating again in a nitrogen-saturated atmosphere, wash and filter the precipitate with a mixture of ethyl acetate/isopropanol in 80:20 ratio and later with ethyl acetate alone. Dry the resulting precipitate in an oven at 40°–50° C. to remove the residual solvents and afterwards place it in a drier in-vacuo on phosphorus pentoxide, until a constant weight is obtained.

The scheme of X-ray diffraction, obtained on the powder as it is (FIG. 1/A), confirms that the resulting compound contains allomorph (A).

Global yield of the process: 94.7%.

EXAMPLE 2

Preparation of allomorph (B) of Z, N-[2-[[[5-(dimethylamino)methyl-2-furanyl]methyl]thio]ethyl]-N'-methyl-2-nitro-1,1-ethenediamine hydrochloride.

Suspend 10.0 g of Z, N-[2-[[[5-(dimethylamino)methyl-2-furanyl] methyl]thio]ethyl]-N'-methyl-2-nitro-1,1-ethenediamine in 100 ml of ethyl acetate. Add dropwise to the mixture 21.95 g of hydrochloric acid (concentration 5.29% mol/mol) in isopropanol, to which the 3% of distilled water was previously added, during 45 minutes, keeping the temperature at 25° C. Stirring vigorously, a white precipitate is obtained. Wash and filter the precipitate with a mixture of ethyl acetate/isopropanol in 80:20 ratio and later with ethyl acetate alone.

Dry the resulting precipitate in an oven at 40°–50° C. to remove the residual solvents and afterwards place it in a drier in-vacuo until a constant weight is obtained.

The scheme of X-ray diffraction, obtained on the powder as it is (FIG. 1/B), confirms that the resulting compound contains allomorph (B).

Global yield of the process: 95.3%.

EXAMPLE 3

Preparation of 100,000 tablets containing 334.8 mg of allomorph (B) of Z, N-[2-[[[5-(dimethylamino)methyl-2-furanyl]methyl] thio]ethyl]-N'-methyl-2-nitro-1,1-ethenediamine hydrochloride [equivalent to 300.0 mg of Z, N-[2-[[[5-(dimethylamino)methyl-2-furanyl]methyl] thio] ethyl]-N'-methyl-2-nitro-1,1-ethenediamine].

All the steps of manufacturing are carried out in rooms with a relative humidity in a range between 40% and 45% and at a temperature between 19° C. and 25° C., sheltered from light. Qualitative and quantitative composition of the tablet of the invention:

| Ingredients | mg/tablet |
|---|---|
| Allomorph (B) of Z, N-[2-[[[5-(dimethylamino] methyl-2-furanyl]methyl]thio]ethyl]-N'-methyl-2-nitro-1,1-ethenediamine hydrochloride (*) | 334.80 |
| microcrystalline cellulose | 210.00 |

-continued

| Ingredients | mg/tablet |
|---|---|
| croscarmellose sodium | 30.00 |
| magnesium stearate | 20.00 |
| silicon dioxide | 12.00 |
| Total weight | 606.80 |

(*) equivalent to 300 mg of Z, N-[2-[[[5-(dimethylamino)methyl-2-furanyl]methyl]thio]ethyl]-N'-methyl-2-nitro-1,1-ethenediamine.

Amounts necessary for the preparation of 100,000 tablets:

| Ingredients | Kg |
|---|---|
| Allomorph (B) of Z, N-[2-[[[5-(dimethylamino)methyl-2-furanyl]methyl]thio]ethyl]-N'-methyl-2-nitro-1,1-ethenediamine hydrochloride | 33.48 |
| microcrystalline cellulose | 21.00 |
| croscarmellose sodium | 3.00 |
| magnesium stearate | 2.00 |
| silicon dioxide | 1.20 |

Introduce in sequence into a suitable mixer for powders 21.0 Kg of microcrystalline cellulose, 2.0 Kg of magnesium stearate, 1.2 Kg of silicon dioxide, 33.48 Kg of allomorph (B) of Z, N-[2-[[[5-(dimethylamino)methyl-2-furanyl]methyl]thio]ethyl]-N'-methyl-2-nitro-1,1-ethenediamine hydrochloride and, finally, 3.0 Kg of croscarmellose sodium.

The mixture of powders is blended until a complete homogeneity is obtained. The resulting mixture of powders is sieved and directly dry-tabletted, without the aid of granulation water, with a conventional tabletting machine equipped with an oblong rounded punch, size 18.5 mm×7.5 mm, optionally with a breaking line on the upper punch, in order to obtain breakable tablets. Each tablet obtained in this way has a unit weight in the range between 637 and 576 mg (±5%). The resulting tablets are then film-coated by procedures already known to the experts.

| | |
|---|---|
| Tablets obtained | n. 95,620 |
| Global yield of the process | 95.62% |

EXAMPLE 4

Preparation of 50,000 ampoules containing 55.80 mg of allomorph (A) of Z, N-[2-[[[5-(dimethylamino)methyl-2-furanyl]methyl]thio] ethyl]-N'-methyl-2-nitro-1,1-ethenediamine hydrochloride [equivalent to 50.0 mg of Z, N-[2-[[[5-(dimethylamino)methyl-2-furanyl]methyl] thio] ethyl]-N'-methyl-2-nitro-1,1-ethenediamine].

Qualitative and quantitative composition of the ampoule of the invention:

| Ingredients | mg/ampoule |
|---|---|
| Allomorph (A) of Z, N-[2-[[[5-(dimethylamino] methyl-2-furanyl]methyl]thio]ethyl]-N'-methyl-2-nitro-1,1-ethenediamine | 55.80 |

| Ingredients | mg/ampoule |
|---|---|
| hydrochloride (*) | |
| Water for injectable preparations (Ph. Eur. III Ed. 2000/USP XXIV) | 5000.00 |
| Hydrochloric acid (Ph. Eur. III Ed. 2000/USP XXIV) | q. s. to pH 5.0 |

(*) equivalent to 50.0 mg of Z, N-[2-[[[5-(dimethylamino)methyl-2-furanyl]methyl]thio]ethyl]-N'-methyl-2-nitro-1,1-ethenediamine.

Amounts necessary to prepare 50,000 ampoules:

| Ingredients | Kg |
|---|---|
| Allomorph (A) of Z, N-[2-[[[5-(dimethylamino)methyl-2-furanyl]methyl]thio]ethyl]-N'-methyl-2-nitro-1,1-ethenediamine hydrochloride | 2.79 |
| Water for injectable preparations (Ph. Eur. III Ed. 2000/USP XXIV) | 250.00 |
| Hydrochloric acid (Ph. Eur. III Ed. 2000/USP XXIV) | q. s. to pH 5.0 |

In a suitable dissolutor for injectable preparations, the active ingredient (2.79 Kg) is dissolved in water for injectable preparations (250.00 Kg) and, when once the operation is concluded, hydrochloric acid is added slowly to the solution until a pH value of about 5.0 is obtained. The solution is saturated with nitrogen and then filtered through a suitable sterilizing filter. Then the solution is introduced into glass ampoules of 5.0 ml (empty volume 7.5 ml) and the ampoules are sealed individually in a nitrogen atmosphere.

| Obtained ampoules | no. 45.358 |
|---|---|
| Global yield of the process | 90.71% |

What is claimed is:

1. Allomorph of Z isomer of N-[2-[[[5-(dimethylamino)methyl-2-furanyl]methyl]thio]ethyl]-N'-methyl-2-nitro-1,1-ethenediamine hydrochloride, with two carbon atoms linked by a rigid ethylenic bond, marked by an asterisk (*), characterized by the following structural formula:

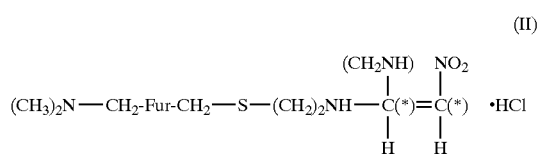

(II)

wherein -Fur- represents a furane ring.

2. Allomorph of Z isomer of N-[2-[[[5-(dimethylamino)methyl-2-furanyl]methyl]thio]ethyl]-N'-methyl-2-nitro-1,1-ethenediamine hydrochloride, as claimed in claim 1, characterized by Z isomer, obtained by reacting selectively the Z isomer of N-methyl-1-methylthio-2-nitroethenamine (I) with 2-[[[5-(dimethylamino) methyl-2-furanyl]methyl]thio]-ethenamine (III), by the following synthesis scheme:

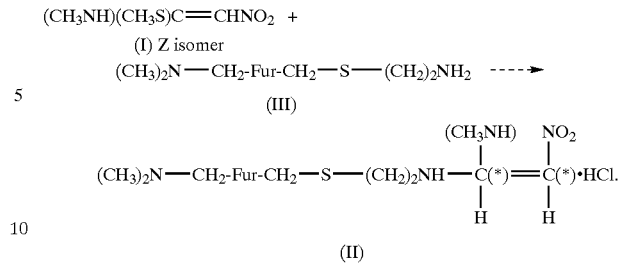

3. Allomorph (A) of the Z isomer of N-[2-[[[5-(dimethylamino)methyl-2-furanyl]methyl]thio]ethyl]-N'-methyl-2-nitro-1,1-ethenediamine hydrochloride, as claimed in claim 1, characterized by the diffractogram shown in FIG. 1/A, obtained on the powder by the adopted method by Debye Scherrer.

4. Allomorph (B) of the Z isomer of N-[2-[[[5-(dimethylamino)methyl-2-furanyl]methyl]thio]ethyl]-N'-methyl-2-nitro-1,1-ethenediamine hydrochloride, as claimed in claim 1, characterized by the diffractogram shown in FIG. 1/B, obtained on the powder by the adopted method by Debye Scherrer.

5. Preparation process of allomorph (A) of Z isomer of N-[2-[[[5-(dimethylamino)methyl-2-furanyl]methyl] thio] ethyl]-N'-methyl-2-nitro-1,1-ethenediamine hydrochloride, characterized by the reaction of Z, N-[2-[[[5-(dimethylamino)methyl-2-furanyl]methyl]thio]ethyl]-N'-methyl-2-nitro-1,1-ethenediamine, suspended in anhydrous ethyl acetate, with a solution of hydrochloric acid in anhydrous isopropanol, added dropwise by keeping the reaction mixture at room temperature.

6. Procedure for the preparation of allomorph (B) of Z isomer of N-[2-[[[5-(dimethylamino)methyl-2-furanyl] methyl]thio]ethyl]-N'-methyl-2-nitro-1,1-ethenediamine hydrochloride, characterized by the reaction of Z, N-[2-[[[5-(dimethylamino)methyl-2-furanyl]methyl]thio] ethyl]-N'-methyl-2-nitro-1,1-ethenediamine, suspended in ethyl acetate, with a solution of hydrochloric acid in isopropanol with 3% of water, added dropwise to the previous one by keeping the reaction mixture at room temperature.

7. Allomorph of Z isomer of N-[2-[[[5-(dimethylamino) methyl-2-furanyl]methyl]thio]ethyl]-N'-methyl-2-nitro-1,1-ethenediamine hydrochloride, as claimed in claim 1, characterized by a greater configuration affinity for histamine $H_2$-receptors.

8. Pharmaceutical composition including the allomorph of Z isomer of N-[2-[[[5-(dimethylamino)methyl-2-furanyl] methyl]thio] ethyl]-N'-methyl-2-nitro-1,1-ethenediamine hydrochloride, as claimed in claim 1, admixed to at least a vehicle or a pharmaceutically acceptable inert diluent, in a suitable form for oral or parenteral administration.

9. Pharmaceutical composition including the allomorph of Z isomer of N-[2-[[[5-(dimethylamino)methyl-2-furanyl] methyl]thio] ethyl]-N'-methyl-2-nitro-1,1-ethenediamine hydrochloride, as claimed in claim 1, associated to an antibiotic or chemotherapeutic agent, particularly useful for the eradication of *Helicobacter pylori*, to be administered by oral route.

* * * * *